United States Patent
Itoh et al.

(10) Patent No.: US 8,945,369 B2
(45) Date of Patent: Feb. 3, 2015

(54) BIOSENSOR MEASUREMENT SYSTEM AND MEASUREMENT METHOD

(75) Inventors: Yoshihiro Itoh, Ehime (JP); Eriko Yamanishi, Ehime (JP); Tsuyoshi Takahashi, Ehime (JP); Hiroyuki Tokunaga, Ehime (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 1179 days.

(21) Appl. No.: 12/375,111

(22) PCT Filed: Jul. 26, 2007

(86) PCT No.: PCT/JP2007/064665
§ 371 (c)(1),
(2), (4) Date: Jan. 26, 2009

(87) PCT Pub. No.: WO2008/013224
PCT Pub. Date: Jan. 31, 2008

(65) Prior Publication Data
US 2010/0000880 A1   Jan. 7, 2010

(30) Foreign Application Priority Data
Jul. 26, 2006 (JP) .................................. 2006-203833

(51) Int. Cl.
C12Q 1/25 (2006.01)
G01N 27/26 (2006.01)
G01N 27/327 (2006.01)

(52) U.S. Cl.
CPC .................................. *G01N 27/3274* (2013.01)
USPC ............. 205/777.5; 204/403.14; 204/403.03; 435/287.2

(58) Field of Classification Search
CPC .................................................. G01N 27/3274
USPC .......... 205/775, 777.5; 204/403.14; 435/287.2
See application file for complete search history.

(56) References Cited

U.S. PATENT DOCUMENTS 5,352,351 A * 10/1994 White et al. ............. 204/403.04
5,653,863 A 8/1997 Genshaw et al.

(Continued)

FOREIGN PATENT DOCUMENTS

EP 0 537 761 4/1993
EP 1 691 192 8/2006

(Continued)

OTHER PUBLICATIONS

International Search Report issued Aug. 21, 2007 in the International (PCT) Application No. PCT/JP2007/064665.

(Continued)

*Primary Examiner* — Luan Van
*Assistant Examiner* — Steven Rosenwald
(74) *Attorney, Agent, or Firm* — Wenderoth, Lind & Ponack, L.L.P.

(57) ABSTRACT

There is provided a biosensor measurement system which can output a highly-precise measurement result even when an impact such as falling of the sensor occurs or the biosensor is an exposed sensor. An abnormal waveform detection electrode is provided in addition to electrodes for quantitative determination of a target substance. Therefore, when an impact is caused by such as falling of the sensor in a halt period where no voltage is applied in a voltage application algorithm, the abnormal waveform detection electrode can detect the impact. Further, also an exposed sensor can be detected by the abnormal waveform which is detected by the abnormal waveform detection electrode.

4 Claims, 7 Drawing Sheets

(56) References Cited

U.S. PATENT DOCUMENTS

| | | | |
|---|---|---|---|
| 6,071,391 A | 6/2000 | Gotoh et al. | |
| 6,156,173 A | 12/2000 | Gotoh et al. | |
| 6,458,258 B2 * | 10/2002 | Taniike et al. | 204/403.14 |
| 6,503,381 B1 | 1/2003 | Gotoh et al. | |
| 6,576,117 B1 * | 6/2003 | Iketaki et al. | 205/777.5 |
| 7,083,712 B2 * | 8/2006 | Morita et al. | 205/775 |
| 2003/0102213 A1 | 6/2003 | Gotoh et al. | |
| 2004/0154932 A1 | 8/2004 | Deng et al. | |
| 2005/0023152 A1 * | 2/2005 | Surridge et al. | 205/775 |
| 2005/0067301 A1 | 3/2005 | Morita et al. | |
| 2005/0258052 A1 | 11/2005 | Gotoh et al. | |
| 2006/0037870 A1 | 2/2006 | Deng et al. | |
| 2009/0205976 A1 * | 8/2009 | Yoshioka et al. | 205/775 |

FOREIGN PATENT DOCUMENTS

| | | | |
|---|---|---|---|
| EP | 1 736 763 | 12/2006 | |
| JP | 04121656 | * 4/1992 | G01N 27/416 |
| JP | 8-502589 | 3/1996 | |
| JP | 8-304340 | 11/1996 | |
| JP | 11-108879 | 4/1999 | |
| JP | 2002-174641 | 6/2002 | |
| JP | 2003-4691 | 1/2003 | |
| JP | 2003-270197 | 9/2003 | |
| JP | 2004-245836 | 9/2004 | |
| WO | 94/29706 | 12/1994 | |
| WO | 99/60391 | 11/1999 | |
| WO | 03/044513 | 5/2003 | |
| WO | 2004/113910 | 12/2004 | |
| WO | 2005/054840 | 6/2005 | |
| WO | 2005/100968 | 10/2005 | |

OTHER PUBLICATIONS

Written Opinion of the ISA issued Aug. 21, 2007 in the International (PCT) Application No. PCT/JP2007/064665.

Extended European Search Report issued Nov. 26, 2013 in corresponding European Application No. 07791365.5.

* cited by examiner

BIOSENSOR MEASUREMENT SYSTEM AND MEASUREMENT METHOD

TECHNICAL FIELD

The present invention relates to a biosensor measurement system and a measurement method and, more particularly, to those capable of detecting an impact due to such as falling of a biosensor.

BACKGROUND ART

There has conventionally been a biosensor in which a sample is introduced into a cavity from a front-end sample supply port by a surfactant layer applied to an upper surface in the cavity. A sensor electrode is composed of a working electrode and a counter electrode, and an oxidation-reduction current value between the counter electrode and the working electrode is measured to determine the quantity of a target substance.

To be specific, many of the conventional biosensors are enzyme sensors using enzymes, and an enzyme sensor is configured such that a working electrode and a counter electrode are placed apart from each other with a predetermined interval and contacting a reduced electron carrier that is obtained by a specific reaction between the target substance and the enzyme, and a voltage is applied between the working electrode and the counter electrode for a predetermined period to oxidize the reduced electron carrier, and a current value (waveform) obtained at this time is measured to determine the quantity of the target substance.

Figure 7:
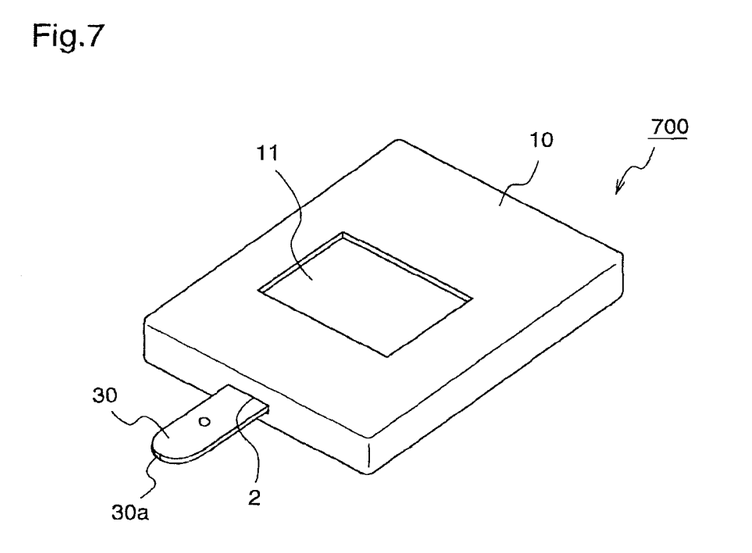
FIG. 7 is a diagram illustrating an example of a conventional biosensor measurement system.

Hereinafter, an example of a biosensor measurement system using an enzyme reaction will be described with reference to FIG. 7.

A biosensor measurement system 700 includes a biosensor 30 having a sample application part 30a at its front end, and a measurement device 10 which measures the concentration of a specific component in a liquid sample applied to the sample application part 30a.

The measurement device 10 includes a support part 2 in which the biosensor 30 is inserted, and a display part 11 which displays the measurement result.

Figure 8:
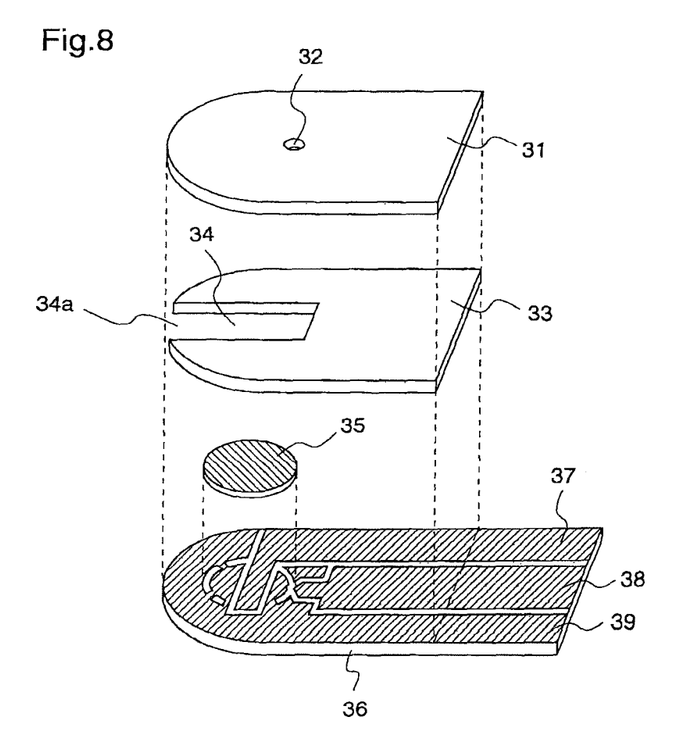
FIG. 8 is an exploded perspective view illustrating an example of a biosensor configuration.

FIG. 8 shows an example of the biosensor 30, which is obtained by laminating a cover 31, a spacer 33, a reagent layer 35, and an insulating substrate 36.

The cover 31 has a vent hole 32 in its center.

The spacer 33 has an approximately rectangular sample supply channel 34.

The reagent layer 35 supports a reagent which enzymatically reacts with the specific component in the liquid sample.

The insulating substrate 36 comprises polyethylene terephthalate or the like, and an electrode layer is formed at its surface. The electrode layer is divided by laser or printing, thereby forming a working electrode 37, a detection electrode 38, and a counter electrode 39.

In the conventional biosensor, a disordered waveform is caused by an external factor such as an impact due to falling of the sensor during measurement, or a procedure of sample application, or a deterioration of the sensor itself due to such as exposure, resulting in abnormal values.

To be specific, in the above-described conventional biosensor, the quantity of electrons on the working electrode dramatically varies and thereby a higher value or a lower value relative to an appropriate response value might be shown in the following cases (1) to (4), resulting in a deterioration of the measurement precision.

(1) when the continuity of the suction of the sample into the cavity is interrupted while applying the sample to the sensor,
(2) when the sample is supplied through an unexpected part such as the vent hole,
(3) when the sample in the cavity is scattered, effused, or flowed out due to an external factor after starting the measurement,
(4) when the preservation state is poor (by such as exposure)

As described above, in the conventional biosensor, the reduced electron carrier substance which is obtained by a specific reaction between the target substance and the enzyme is oxidized by applying a voltage between the working electrode and the counter electrode for a predetermined period, and the obtained current value (waveform) is measured to determine the quantity of the target substance. However, since the conventional self monitoring blood-glucose biosensor comprising the sensor and the measurement device is very small in size, it might be dropped due to faulty operation or the like.

Further, in the biosensor, a disordered waveform (abnormal waveform) is caused by an external factor such as an impact due to falling of the sensor or a procedure of sample application during the measurement time, and thereby the measured value is significantly deviated from the true value.

The conventional biosensors as described above are disclosed in the following documents.

Patent Document 1: Japanese Published Patent Application No. 2004-245836
Patent Document 2: Japanese Published Patent Application No. 2003-4691
Patent Document 3: Japanese Published Patent Application No. Hei. 8-304340
Patent Document 4: International Publication WO 99/60391
Patent Document 5; National Publication of Translated Version No. 8-502589

SUMMARY OF THE INVENTION

Problems to be Solved by the Invention

In the above-described conventional biosensors, there are cases where the quantity of electrons on the working electrode dramatically varies and thereby a higher value or a lower value relative to the appropriate response value might be shown. This results in a deterioration of the measurement precision and one reason for market claims.

In order to eliminate abnormal values due to such abnormal waveform, it is necessary to constantly monitor the abnormal waveform during the measurement.

However, in an optimum algorithm used for performing quantitative determination on a usual target substance, an algorithm in which no voltage is applied is often provided, where no measurement of current can be performed, and thereby it was not possible to perform detection of an abnormal waveform.

The present invention is made to solve the above-described problems and has for its object to provide a biosensor measurement system and a measurement method having high measurement precision, which can eliminate the measurement results that are obtained when an impact due to such as falling of the biosensor occurs, or under other abnormal conditions.

Measures to Solve the Problems

In order to solve the above-described problems, according to a first aspect of the present invention, there is provided a measurement method using a biosensor having a first electrode system for measuring a target substance, which comprises a working electrode and a counter electrode, and a reagent layer containing an oxidation-reduction enzyme for oxidizing or reducing the target substance, which is disposed in the vicinity of the first electrode system, the method including the steps of applying a voltage to the first electrode system after a liquid sample is introduced onto the first electrode system, detecting an oxidation-reduction current that is generated by the voltage application, and converting the current value into the quantity of the target component, wherein the biosensor has, in addition to the first electrode system, a second electrode system for abnormality detection which comprises a working electrode and a counter electrode, and a voltage is applied to the second electrode system during the measurement period so as to detect an abnormal waveform current during the measurement period.

According to a second aspect of the present invention, a voltage application pattern to the first electrode system has a halt period when no voltage is applied.

According to a third aspect of the present invention, a voltage is continuously applied to the second electrode system during the measurement period.

According to a fourth aspect of the present invention, a constant voltage is continuously applied to the second electrode system during the measurement period.

According to a fifth aspect of the present invention, the current waveform of the second electrode system is monitored to detect an abnormal waveform.

According to a sixth aspect of the present invention, a predetermined threshold range is set when monitoring the current waveform of the second electrode system, and the monitored waveform is judged as an abnormal waveform when the waveform is outside the threshold range.

According to a seventh aspect of the present invention, the predetermined threshold range is set based on normal measurement response values, or it is set using differences of the response values between the respective measurement points.

According to an eighth aspect of the present invention, there is provided a biosensor measurement system having a biosensor including a first electrode system for measuring a target component, which comprises a working electrode and a counter electrode, and a reagent layer containing at least an oxidation-reduction enzyme for oxidizing or reducing a specific target component, which is disposed in the vicinity of the first electrode system, the biosensor applying a voltage to the first electrode system after a liquid sample is introduced onto the first electrode system, detecting an oxidation-reduction current that is generated by the voltage application, and converting the current value into the quantity of the target component to determine the quantity of the target component, wherein the biosensor further includes, in addition to the first electrode system, a second electrode system for abnormality detection which comprises a working electrode and a counter electrode, and the second electrode system is supplied with a voltage during the measurement period so as to detect an abnormal current during the measurement period.

According to a ninth aspect the present invention, the second electrode system shares its counter electrode with the first electrode system.

According to a tenth aspect of the present invention, at least the working electrode of the second electrode system is disposed so as not to contact with the reagent layer.

According to an eleventh aspect of the present invention, at least the working electrode of the second electrode system is placed at an upper position in the stream of introducing the liquid sample than the first electrode system.

According to a twelfth aspect of the present invention, the electrodes constituting the second electrode system are also used as a sample detection electrode, a hematocrit correction electrode, or an interfering substance correction electrode other than the first electrode system.

Effects of the Invention

According to the present invention, there is provided a biosensor measurement system which includes a target substance measurement electrode system comprising a working electrode and a counter electrode, and applies a voltage to the target substance measurement electrode system using a predetermined voltage application pattern to output an oxidation-reduction current measurement value obtained during the voltage application period, and the biosensor measurement system further includes, in addition to the target substance measurement electrode, an abnormal waveform detection electrode system for detecting an abnormal waveform, and detects an abnormal waveform using the abnormal waveform detection electrode system. Therefore, when an output of a normal measurement value cannot be expected in the following cases (1) to (4):

(1) when the continuity of the suction of the sample into the cavity is interrupted due to such as additional application while applying the sample to the sensor, (2) when the sample is supplied through an unexpected part such as the vent hole, (3) when the sample in the cavity is scattered, effused, or flowed out due to an external factor after starting the measurement, (4) when the preservation state is poor due to such as exposure error display is performed or outputting of the measurement value is not performed based on the abnormality detected, and thereby the measurement precision of the biosensor is significantly enhanced.

BRIEF DESCRIPTION OF THE DRAWINGS

FIG. 2 is a diagram illustrating the configurations of electrodes in the biosensor measurement system of the first embodiment, wherein FIG. 2(a) shows the electrode configuration in a biosensor 100 of a first example of the first embodiment, FIG. 2(b) shows the electrode configuration in a biosensor 200 of a second example of the first embodiment, and FIG. 2(c) shows the electrode configuration in a biosensor 300 of a third example of the first embodiment.

FIG. 5 is a diagram illustrating the measurement result of the first example (<detection of abnormal waveform due to impact>) of the first embodiment, wherein

FIG. 6 is a diagram illustrating the measurement result of the second example (<detection of abnormal waveform due to exposed sensor>) of the first embodiment, wherein FIG. 6(a)

shows a measurement electrode current value.

DESCRIPTION OF REFERENCE NUMERALS

A . . . working electrode
B . . . sample detection electrode
C . . . counter electrode
D . . . abnormal waveform detection electrode
E . . . hematocrit correction electrode or interfering substance correction electrode
100 . . . biosensor
200 . . . biosensor
300 . . . biosensor
400 . . . measurement device
C1, C2, C3, C4 . . . connectors
SW . . . switching circuit
40 . . . reference voltage supply
41 . . . current/voltage conversion circuit
42 . . . A/D conversion circuit
43 . . . CPU
44 . . . display part comprising a liquid crystal display (LCD)
Tu, Tl . . . upper and lower threshold values
R . . . threshold range
700 . . . biosensor measurement system
30 . . . biosensor
30a . . . sample application part
31 . . . cover
32 . . . vent hole
33 . . . spacer
34 . . . sample supply channel
34a . . . sample supply port
35 . . . reagent layer
36 . . . insulating substrate
37 . . . working electrode
38 . . . detection electrode
39 . . . counter electrode

DETAILED DESCRIPTION OF THE INVENTION

Hereinafter, an embodiment of the present invention will be described with reference to the drawings.
(Embodiment 1)

Hereinafter, a description will be given of a biosensor measurement system according to a first embodiment of the present invention, and a method for detecting an abnormal waveform in a biosensor. In this first embodiment, a blood glucose sensor which adopts blood as a sample to measure the glucose concentration in blood.

Figure 1:
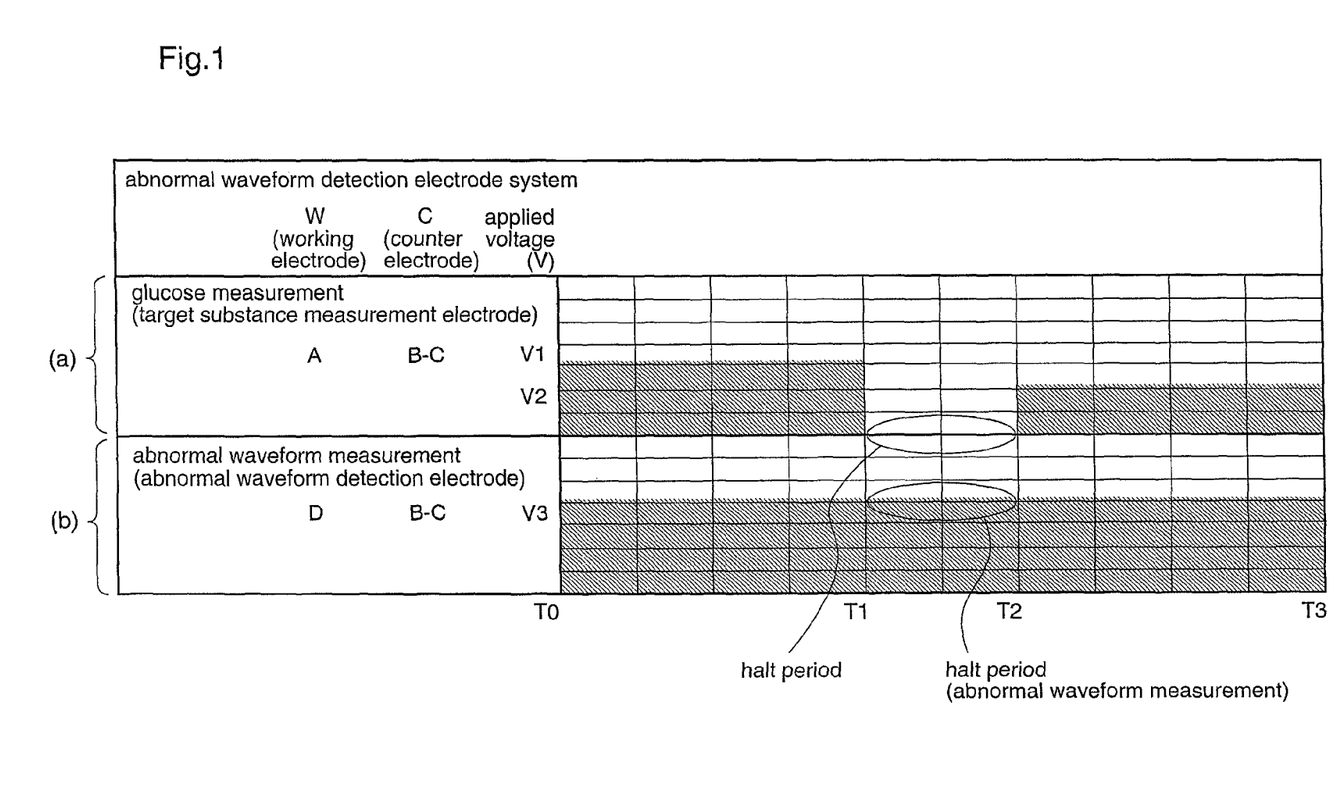
FIG. 1 is a diagram illustrating a voltage application algorithm used for target substance measurement and abnormal waveform detection in a biosensor measurement system according to the first embodiment of the present invention.

FIG. 1 is a diagram illustrating voltage application algorithms for a target substance measurement electrode and an abnormal waveform detection electrode in the biosensor measurement system of this first embodiment.

As shown in FIG. 1(a), in the measurement of glucose as a target substance according to the conventional art, since the measurement algorithm has a halt period during which no voltage is applied between a first voltage application period T0-T1 (application voltage V1) and a second voltage application period T2-T3 (application voltage V2), no oxidation current is measured in the glucose measurement during the halt period T1-T2.

Since no voltage is applied during the halt period T1-T2, no voltage flows between the electrodes. Therefore, even when an impact or the like occurs due to such as falling of the sensor, the electrodes cannot detect the impact during this halt period.

On the other hand, in the abnormal waveform monitoring output shown in FIG. 1(b), since a voltage of V3 is constantly applied to the abnormal waveform detection electrode to perform monitoring of abnormal waveforms, abnormal waveform monitoring output is performed throughout the period from the voltage application start time T0 to the voltage application end time T3.

Figure 2:
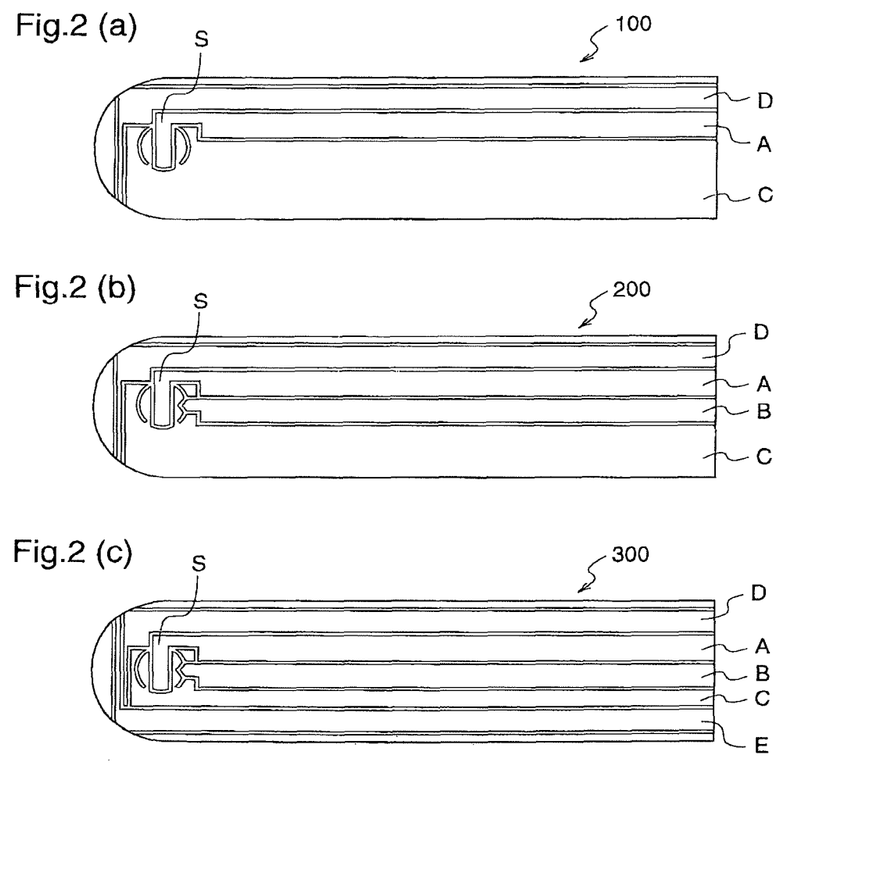

FIG. 2 is a diagram illustrating the configuration of the electrodes in the biosensor of this first embodiment. The fundamental configuration such as the arrangement of the cover, the spacer, the reagent, and the sample supply port is identical to that of the conventional biosensor.

FIG. 2(a) shows an electrode configuration in a first example 100 of the first embodiment, wherein A is a working electrode and C is a counter electrode. At least a reagent layer (not shown) for oxidizing or reducing a specific target component is disposed on these target substance measurement electrodes A and C. In the figure, S shows the reagent layer placement position.

Further, D shows an abnormal waveform detection electrode. Since this abnormal waveform detection electrode D is disposed so as not to contact the reagent layer, only detection of an abnormal waveform can be carried out without affected by a reduced electron carrier substance which is caused by a reaction between the target substance and the reagent.

Further, the abnormal waveform detection electrode D is desirably disposed upstream the target substance measurement electrodes A and C, i.e., on the sample supply port (not shown) side which exists at the apex of the semicircular shape, in order to prevent the electrode D from being affected by the reduced electron carrier substance which is caused by the reaction between the target substance and the reagent.

FIG. 2(b) shows an electrode configuration of a second example 200 of the first embodiment, wherein A is a working electrode, B is a sample detection electrode, and C is a counter electrode. A reagent layer (not shown) is disposed on these target substance measurement electrodes A, B, and C.

Further, D is an abnormal waveform detection electrode. Since this abnormal waveform detection electrode D is disposed so as not to contact the reagent layer, only detection of an abnormal waveform can be carried out without affected by a reduced electron carrier substance which is caused by a reaction between the target substance and the reagent.

Further, as in the first example, the abnormal waveform detection electrode D is desirably disposed upstream the target substance measurement electrodes A, B, and C, i.e., on the sample supply port (not shown) side which exists at the apex of the semicircular shape, in order to prevent the electrode D from being affected by the reduced electron carrier substance which is caused by the reaction between the target substance and the reagent.

Furthermore, the abnormal waveform detection electrode system may share its counter electrode with the target substance measurement electrode system.

FIG. 2(c) shows an electrode configuration of a third example 300 of the first embodiment, wherein A, B, C, and D are identical to those of the second example 200.

In this third example 300, a hematocrit correction electrode or an interfering substance correction electrode is provided as an electrode E. Further, the abnormal waveform detection electrode may be implemented by the same electrode as the sample detection electrode, or the hematocrit correction electrode, or the interfering substance correction electrode other than the target substance measurement electrode. In this case, the biosensor can be easily configured.

Figure 3:
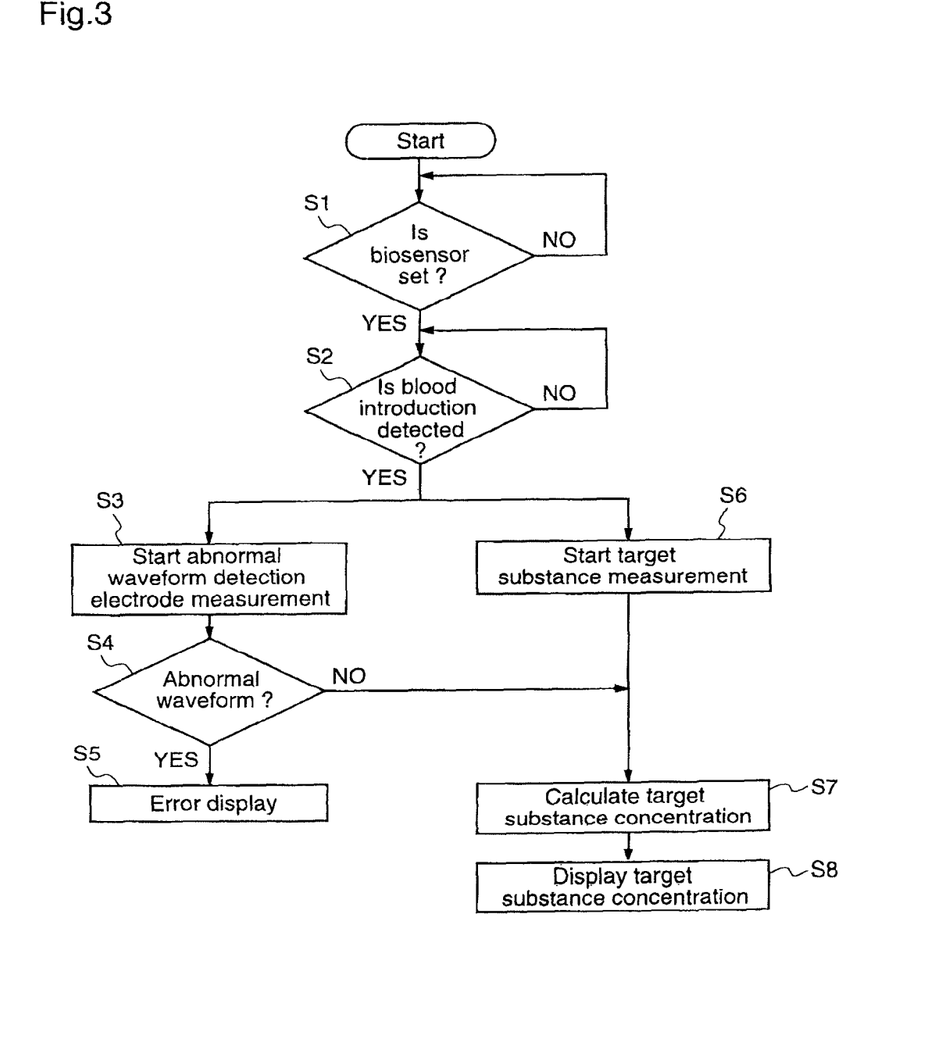
FIG. 3 is a diagram illustrating a detection flow in a biosensor abnormal waveform detection method according to the first embodiment of the present invention.

FIG. 3 is a diagram illustrating a detection flow in the biosensor abnormal waveform detection method of the first embodiment of the present invention. In FIG. 3, S1 is a step of judging whether the biosensor is set or not, S2 is a step of judging whether introduction of blood is detected or not, S3 is a step of starting measurement by the abnormal waveform detection electrode when the judgment result in the judgment step S2 is "Yes", S4 is a step of judging whether an abnormal waveform is detected or not, S5 is a step of performing error display when the judgment result in the judgment step S4 is "Yes", 56 is a step of starting measurement of the target substance simultaneously with the measurement start step S3 by the abnormal waveform detection electrode when the judgment result in the judgment step S2 is "Yes", S7 is a step of calculating the concentration of the target substance after the step S6, and S8 is a step of displaying the concentration of the target substance.

Figure 4:
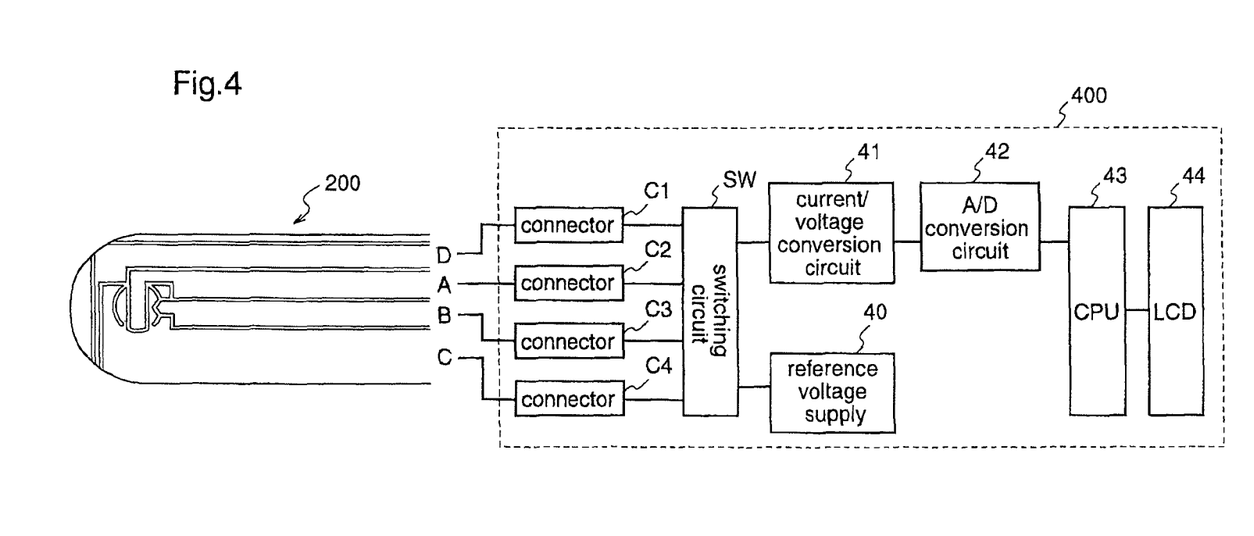
FIG. 4 is a diagram illustrating the electrode configuration of the biosensor 200 of the second example of the first embodiment and the block configuration of a measurement device 400.

FIG. 4 is a diagram illustrating the electrode configuration of the biosensor 200 (second example) and the block configuration of the measurement device 400 which are the constituents of the biosensor measurement system of the first embodiment.

In the biosensor 200, A, B, C, and D denote a working electrode, a sample detection electrode, a counter electrode, and an abnormal waveform detection electrode, respectively.

In the measurement device 400, C1, C2, C3, and C4 denote connectors, SW denotes a switching circuit, 40 denotes a reference voltage supply, 41 denotes a current/voltage conversion circuit, 42 denotes an A/D conversion circuit, 43 denotes a CPU, and 44 denotes a display part comprising a liquid crystal display (LCD).

The connectors C1, C2, C3, and C4 contact the working electrode A, the detection electrode B, the counter electrode C, and the abnormal waveform detection electrode D of the biosensor 200, respectively.

The reference voltage supply 40 applies a voltage between the connectors C1, C2, C3, and C4. The switching circuit SW changes the connections between the connectors C1, C2, C3, C4, and the reference voltage supply 40, and the connections between the connectors C1, C2, C3, C4, and the current/voltage conversion circuit 41.

The current/voltage conversion circuit 41 converts the currents flowing through the respective electrode systems into voltages.

The A/D conversion circuit 42 converts the output values from the current/voltage conversion circuit 41 into pulses.

The CPU 43 calculates the concentration of the specific component in the liquid sample, for example, the concentration of glucose, on the basis of the pulses outputted from the A/D conversion circuit 42.

The display part 44 comprising an LCD or the like displays the calculation result obtained by the CPU 43 such as the glucose concentration.

Hereinafter, a description will be given of Example 1 (<detection of abnormal waveform due to impact>) and Example 2 (<detection of abnormal waveform due to exposed sensor>) according to the first embodiment.

EXAMPLE 1

Detection of Abnormal Waveform Due to Impact

Details of Experiment
Sensor: The sensor 200 and the measurement device 400 of the above-described configurations are used.
Measurement profile: The application algorithm (total measurement time=5 sec) shown in FIG. 1 is used.
Measurement ambient: 25° C.
Sample: glucose standard solution (pseudo sample aqueous solution having known glucose concentration)
Abnormal measurement: An impact is given to the sensor with a fingertip after sample detection.
Normal measurement: The sensor is left standstill after sample detection.
Contents of Experiment and Result of Experiment
This experiment performs a comparison between the normal measurement and the abnormal measurement in which an impact is artificially given.

The response value of the abnormal waveform detection electrode in the abnormal measurement deviates from the waveform obtained in the normal measurement at the point of 2.9 sec. when an impact is given, and therefore, the abnormal waveform detection electrode detects the impact by the fingertip.

However, since the point of 2.9 sec. is in the voltage application halt period for the glucose measurement electrode, the glucose measurement electrode cannot detect the abnormal waveform due to the impact.

In the conventional art which cannot detect the abnormal waveform, since the glucose concentration is calculated from the deviated final response value, an abnormal value is displayed.

A threshold range R is determined (normal measurement response value ±0.65 µA) based on the normal measurement response value which is obtained when using the abnormal waveform detection electrode of the present invention.

Since the response value of the abnormal waveform detection electrode in the abnormal measurement is outside the set threshold range at the point of 2.9 sec. when the impact is given, it can be judged as an abnormal waveform.

Since, in this example, the response value of the abnormal waveform detection electrode obtained by the abnormal measurement significantly deviates from the response value obtained by the normal measurement, the threshold range R can be set at the normal measurement ±10 S.D. considering the standard deviation (S.D.) at the normal measurement, and thereby the abnormal waveform can be detected without falsely judging the normal measurement as the abnormal measurement (false judgment rate: $1.5 \times 10^{-21}$%).

When the response value of the abnormal waveform detection electrode by the abnormal waveform overlaps the threshold range (normal measurement ±10 S.D.) and thereby it is difficult to discriminate the abnormal measurement from the normal measurement, the threshold range may be set at normal measurement ±6 S.D. or ±3 S.D. as needed.

When an abnormal waveform is detected by the abnormal waveform detection electrode, the abnormal value is eliminated by error display.

While the respective measurement points are set at intervals of 0.1 sec., intervals of about 0.05 sec. are desirable for further enhancement of the detection precision. Further, in order to enhance the precision of the waveform obtained, it is desired to continuously apply a constant voltage to the abnormal waveform detection electrode during the measurement period.

Figure 5A:
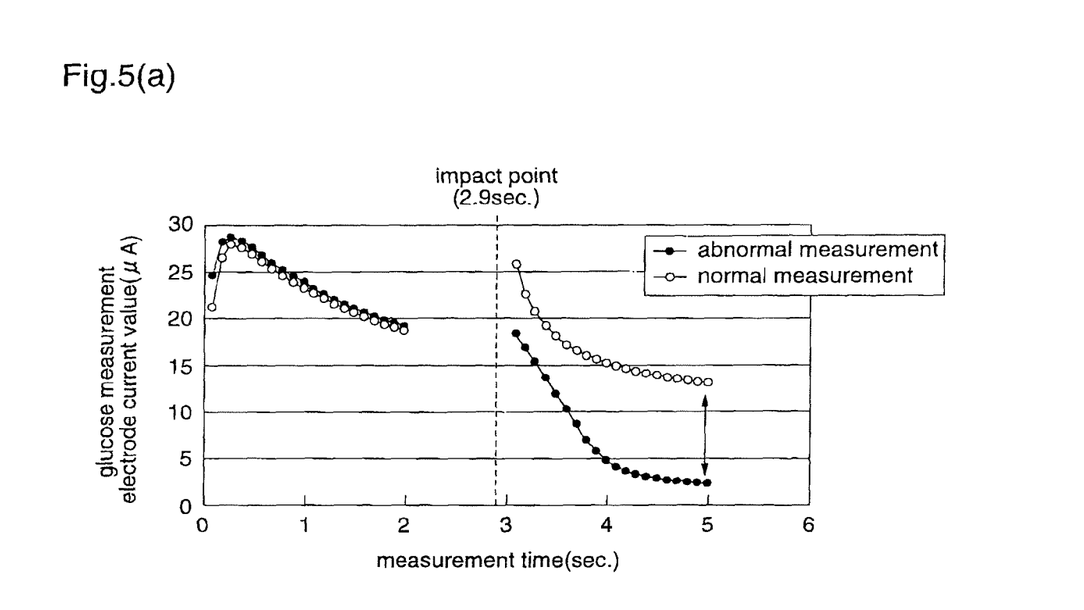
FIG. 5(a) shows a measurement electrode current value.
Figure 5B:
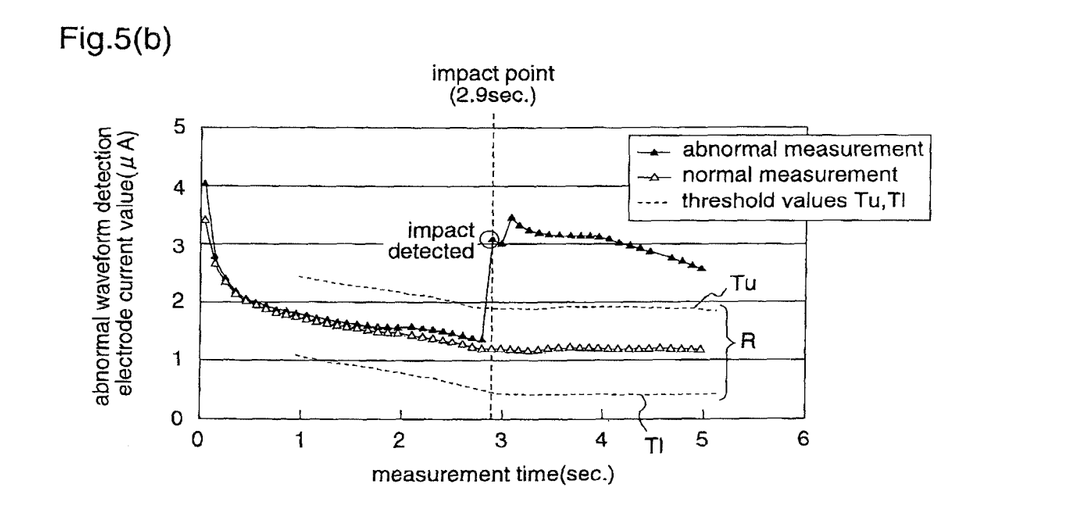
FIG. 5(b) shows an abnormal waveform detection electrode current value.

FIG. 5 shows the measurement results of Example 1 (<detection of abnormal waveform due to impact>) of the first embodiment, wherein FIG. 5(a) shows the measurement electrode current value and FIG. 5(b) shows the abnormal waveform detection electrode current value.

In FIG. 5(a), the abscissa shows the measurement time while the ordinate shows the glucose measurement electrode current value (μA), and ○ dots show the normal measurement while ● dots show the abnormal measurement.

In FIG. 5(b), the abscissa shows the measurement time while the ordinate shows the abnormal waveform detection electrode current value (μA), Δ dots show the normal measurement while ▲ dots show the abnormal measurement, broken lines show the upper threshold value Tu and the lower threshold value Tl, and a threshold range R is determined by the upper threshold value Tu and the lower threshold value Tl.

To be specific, in Example 1 (<detection of abnormal waveform due to impact>), when an impact occurs at the time of 2.9 sec. in FIGS. 5(a) and 5(b), the curve of the waveform shown by ● marks is smooth in the glucose measurement electrode current waveform shown in FIG. 5(a), that is, the transition of the current value during the abnormal measurement shown by ● marks is smooth. Therefore, it is not possible to immediately judge that an impact such as falling of the sensor occurred, by seeing the curve of the waveform of ● marks.

Since the presence of the impact cannot be judged, the measured current value of the waveform of ● marks obtained when the voltage application is ended (time T3, i.e., 5 sec.) significantly deviates from the current value obtained by the normal measurement of the sensor shown by ○ marks, but it is not desirable to recognize the measured current value of ● marks as the measured current value in the normal state.

In the present invention, however, it is possible to judge that there was an impact such as falling of the sensor by seeing the waveform of the abnormal waveform detection electrode current value (transition of the current value shown by ▲ marks) shown in FIG. 5(b).

That is, at this time, the current value of the abnormal waveform detection electrode (the current value shown by ▲ marks) shown in FIG. 5(b) jumps from 1.32 μA to 3.05 μA at the point around 2.9 sec., and it is possible to judge by this "jumping" in the waveform that, also in FIG. 5(a), there was an abnormality due to an impact at the point around 2.9 sec. in the period from T1 (2 sec) to T2 (3 sec) where no output is detected

EXAMPLE 2

Detection of Abnormal Waveform Due to Exposed Sensor

Details of Experiment
Sensor: The sensor 200 and the measurement device 400 of the above-described configurations are used.
Measurement profile: The application algorithm (total measurement time=5 sec.) shown in FIG. 1 is used.
Measurement ambient: 25° C.
Sample: glucose standard solution (pseudo sample aqueous solution having known glucose concentration)
Exposed sensor: A deteriorated sensor which has been exposed under an ambient of 40° C./humidity 80% for 24 hours is used.
Normal sensor: A normal sensor which is not deteriorated is used.

Contents of Experiment and Results of Experiment
This experiment performs measurements of the exposed sensor and the normal sensor.

In the conventional art, the response value of the glucose measurement electrode in the exposed sensor is increased due to the deterioration of the sensor, and the response value deviates from that obtained by the normal sensor to display an abnormal value.

When the exposed sensor is measured by the abnormal waveform detection electrode of the present invention, the response value deviates from that of the normal sensor because the condition of the reagent is changed due to the exposure.

A threshold value is set (normal measurement response value ±0.65 μA) based on the response value of the abnormal waveform detection electrode of the normal sensor.

Since the response value of the abnormal waveform detection electrode obtained during the exposed sensor measurement is outside the threshold range, it can be judged as an abnormal waveform.

When the abnormal waveform is detected by the abnormal waveform detection electrode, the abnormal value is eliminated by error display.

Figure 6A:
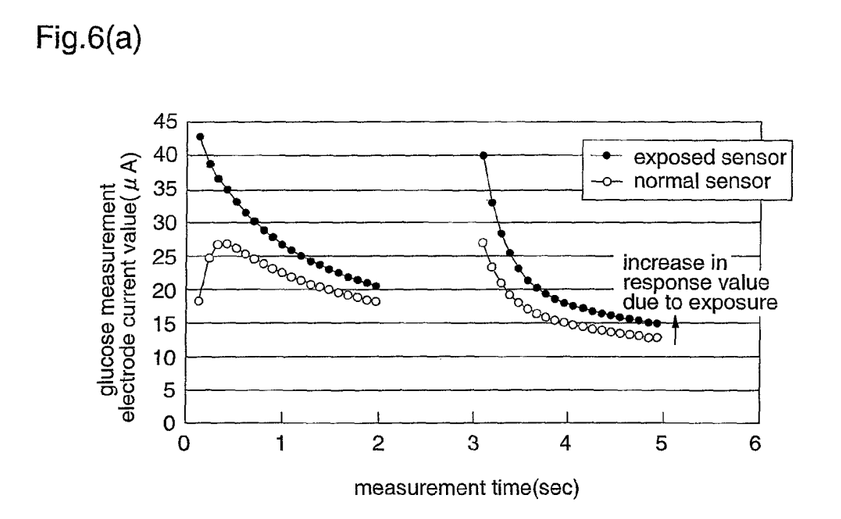
Figure 6B:
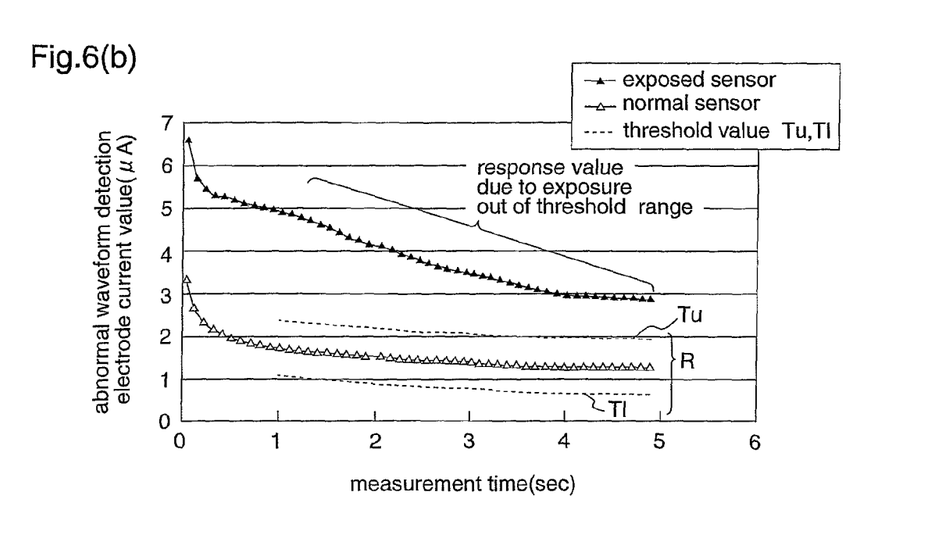
FIG. 6(b) shows an abnormal waveform detection electrode current value.

FIG. 6 shows the measurement result of Example 2 (<detection of abnormal waveform due to exposed sensor>) of the first embodiment, wherein FIG. 6(a) shows the measurement electrode current value and FIG. 6(b) shows the abnormal waveform detection electrode current value.

In FIG. 6(a), the abscissa shows the measurement time while the ordinate shows the glucose measurement electrode current value (μA), and ○ dots show the normal sensor while ● dots show the exposed sensor.

Further, in FIG. 6(b), the abscissa shows the measurement time while the ordinate shows the abnormal waveform detection electrode current value (μA), Δ dots show the normal sensor while ▲ dots show the exposed sensor, broken lines show the upper threshold value Tu and the lower threshold value Tl, and a threshold range R is determined by the upper threshold value Tu and the lower threshold value Tl.

That is, in Example 2 (<detection of abnormal waveform due to exposed sensor>), the results shown in FIGS. 6(a) and 6(b) are obtained by performing measurements of the exposed sensor and the normal sensor, and the followings are found.

That is, in the conventional art, the response value of the glucose measurement electrode of the exposed sensor is increased due to the deterioration of the sensor, and thereby the response value deviates from the response value of the glucose measurement electrode of the normal sensor to show the abnormal value.

On the other hand, when the exposed sensor is measured by the abnormal waveform detection electrode of the present invention, the response value deviates from that of the normal sensor because the condition of the reagent is changed due to the exposure.

Accordingly, by setting a threshold range to, for example, ±0.65 μA of the response value of the normal measurement on the basis of the response value of the abnormal waveform detection electrode of the normal sensor, the response value of the abnormal waveform detection electrode obtained in the exposed sensor measurement can be judged as an abnormal waveform if the response value exceeds this threshold range, and thereby the sensor can be judged as an exposed sensor.

When the abnormal waveform is thus detected by the abnormal waveform detection electrode, error display is carried out and the abnormal value is eliminated.

According to the biosensor measurement system of the first embodiment, since the abnormal waveform detection electrode is newly provided in addition to the electrodes for target substance quantitation, when an impact due to such as falling of the sensor occurs in the halt period where no voltage is applied in the voltage application algorithm, the abnormal waveform detection electrode can detect this impact, and furthermore, even an exposed sensor can be detected by the abnormal waveform which is detected by the abnormal waveform detection electrode.

While in the first embodiment blood glucose is adopted as the measurement target substance, the measurement target substance is not restricted to blood glucose, and it may be a biological sample such as cholesterol, triglyceride, lactic acid, uric acid, bilirubin, or alcohol, an ambient sample, or a food sample may be adopted with the same effects as described above.

Applicability in Industry

According to the present invention, a self monitoring blood-glucose biosensor having high measurement precision can be obtained at reduced cost, and it is useful in hospitals, homes, and the like.

The invention claimed is:

1. A measurement method using a biosensor having (i) a first electrode system for measuring a target substance, the first electrode system including a working electrode and a counter electrode, and (ii) a reagent layer containing an oxidation-reduction enzyme for oxidizing or reducing the target substance, the reagent layer being disposed in a vicinity of the first electrode system, said measurement method comprising:
   applying a voltage to the first electrode system after a liquid sample is introduced onto the first electrode system;
   detecting an oxidation-reduction current that is generated by said applying the voltage; and
   converting a value of the oxidation-reduction current into a quantity of the target component,
   wherein the biosensor has a second electrode system for abnormal current waveform detection, the second electrode system including a working electrode and a counter electrode,
   wherein a voltage application pattern applied to the first electrode system has a first voltage application, a second voltage application, and a halt period between the first voltage application and the second voltage application when no voltage is applied,
   wherein a voltage is continuously applied to the second electrode system during a measurement period corresponding to the first voltage application, the halt period, and the second voltage application when the first electrode system detects the quantity of the target component so as to monitor a current waveform of the second electrode system to detect an abnormal current waveform during the measurement period,
   wherein the abnormal current waveform is caused by an external factor of an impact to the biosensor or a falling impact, and
   wherein the biosensor is included in a biosensor measurement system having a reference voltage supply and a switching circuit for (i) applying the voltage to the first electrode system according to the voltage application pattern applied to the first electrode system having the halt period when no voltage is applied and (ii) continuously applying the voltage to the second electrode system during the measurement period and the halt period.

2. A measurement method as defined in claim 1,
wherein a constant voltage is continuously applied to the second electrode system during the measurement period.

3. A measurement method as defined in claim 1,
wherein a predetermined threshold range is set when monitoring the current waveform of the second electrode system, and
wherein the monitored waveform is judged as the abnormal current waveform when the current waveform is outside the predetermined threshold range.

4. A measurement method as defined in claim 3,
wherein the predetermined threshold range is set based on normal measurement response values, or the predetermined threshold range is set using differences of response values between respective measurement points.

* * * * *